(12) United States Patent
Rohaly et al.

(10) Patent No.: US 8,830,309 B2
(45) Date of Patent: Sep. 9, 2014

(54) HIERARCHICAL PROCESSING USING IMAGE DEFORMATION

(75) Inventors: Janos Rohaly, Acton, MA (US); Ilya A. Kriveshko, Littleton, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 341 days.

(21) Appl. No.: 12/811,236

(22) PCT Filed: Jan. 4, 2009

(86) PCT No.: PCT/US2009/030067
§ 371 (c)(1),
(2), (4) Date: Sep. 22, 2010

(87) PCT Pub. No.: WO2009/089128
PCT Pub. Date: Jul. 16, 2009

(65) Prior Publication Data
US 2011/0007137 A1    Jan. 13, 2011

Related U.S. Application Data

(60) Provisional application No. 61/019,159, filed on Jan. 4, 2008.

(51) Int. Cl.
*H04N 13/02* (2006.01)
*A61C 13/00* (2006.01)
*G06K 9/00* (2006.01)
*G06T 17/00* (2006.01)

(52) U.S. Cl.
CPC ............ *G06T 17/00* (2013.01); *A61C 13/0004* (2013.01); *G06K 9/00214* (2013.01); *H04N 13/0221* (2013.01); *G06T 2207/10012* (2013.01); *G06T 2210/41* (2013.01); *G06K 9/00201* (2013.01)

USPC ............ 348/66; 382/154; 382/285; 382/299; 433/213; 345/419

(58) Field of Classification Search
CPC ............... G06T 2207/10012; H04N 19/00278; H04N 19/00096; H04N 13/0239; H04N 2013/0081; H04N 13/0296
USPC ................. 348/42, 51, E13.005; 433/29, 215
IPC ....................... H04N 13/04, 15/00; G06T 15/00
See application file for complete search history.

(56) References Cited

U.S. PATENT DOCUMENTS 5,727,078 A * 3/1998 Chupeau ........................ 382/154
5,963,664 A * 10/1999 Kumar et al. ................. 382/154

(Continued)

FOREIGN PATENT DOCUMENTS

KR    2007-0039641    4/2007

OTHER PUBLICATIONS

Zhang, Liang. "Hierarchical block-based disparity estimation using mean absolute difference and dynamic programming." Proc. International Workshop on Very Low Bitrate Video Coding. 2001.*

(Continued)

*Primary Examiner* — Jay Patel
*Assistant Examiner* — Neil Mikeska (57) ABSTRACT

A hierarchical pattern matching process is improved for use in three-dimensional reconstruction by calculating a disparity field for low-resolution data, and using this low-resolution disparity field to estimate the disparity field for higher-resolution images. By pre-warping a template according to the estimated disparity field, improved correlation results can be obtained.

20 Claims, 5 Drawing Sheets

(56) References Cited

U.S. PATENT DOCUMENTS

| | | |
|---|---|---|
| 6,208,347 B1 | 3/2001 | Migdal et al. |
| 6,219,437 B1 | 4/2001 | Baldur |
| 6,973,204 B2 | 12/2005 | Adachi |
| 7,085,323 B2 | 8/2006 | Hong |
| 7,372,642 B2 | 5/2008 | Rohaly |
| 7,508,430 B1 | 3/2009 | Oten et al. |
| 7,605,817 B2 | 10/2009 | Zhang et al. |
| 8,073,190 B2 | 12/2011 | Gloudemans |
| 8,467,628 B2 | 6/2013 | Coffman |
| 2001/0016063 A1 | 8/2001 | Albeck et al. |
| 2001/0033326 A1* | 10/2001 | Goldstein et al. ............... 348/42 |
| 2001/0036307 A1* | 11/2001 | Hanna et al. .................. 382/154 |
| 2002/0136444 A1 | 9/2002 | Brown et al. |
| 2003/0190072 A1* | 10/2003 | Adkins et al. ................. 382/154 |
| 2004/0051783 A1 | 3/2004 | Chellappa et al. |
| 2004/0151401 A1* | 8/2004 | Sawhney et al. ............. 382/299 |
| 2004/0197728 A1 | 10/2004 | Abolfathi et al. |
| 2005/0089213 A1* | 4/2005 | Geng .......................... 382/154 |
| 2005/0089214 A1 | 4/2005 | Rubbert et al. |
| 2005/0089822 A1 | 4/2005 | Geng |
| 2005/0182295 A1 | 8/2005 | Soper et al. |
| 2005/0201612 A1* | 9/2005 | Park et al. ..................... 382/154 |
| 2005/0285874 A1 | 12/2005 | Zitnick, II et al. |
| 2006/0066612 A1* | 3/2006 | Yang et al. .................... 345/419 |
| 2006/0154198 A1* | 7/2006 | Durbin et al. .................. 433/29 |
| 2006/0204076 A1 | 9/2006 | Avanish et al. |
| 2006/0208927 A1 | 9/2006 | Poor et al. |
| 2006/0262856 A1* | 11/2006 | Wu et al. .................. 375/240.19 |
| 2007/0031064 A1* | 2/2007 | Zhao et al. ..................... 382/285 |
| 2007/0103460 A1 | 5/2007 | Zhang et al. |
| 2007/0127813 A1 | 6/2007 | Shah |
| 2007/0141534 A1* | 6/2007 | Wen ............................. 433/213 |
| 2007/0172101 A1 | 7/2007 | Kriveshko et al. |
| 2007/0172112 A1 | 7/2007 | Paley et al. |
| 2007/0253618 A1 | 11/2007 | Kim et al. |
| 2008/0025646 A1 | 1/2008 | Aguera y Arcas et al. |
| 2008/0238916 A1 | 10/2008 | Ghosh et al. |

OTHER PUBLICATIONS

Dorst, "First Order Propagation of the Procrustes Method for 3D Attitude Estimation", IEEE Transactions on Pattern Analysis and Machine Intelligence, vol. 27, No. 2, Feb. 2005, pp. 221-229.

Zhang, "Hierarchical Block-Based Disparity Estimation Using Mean Absolute Difference and Dynamic Programming", Proc. of the Int. Workshop on Very Low Bitrate Video Coding, pp. 114, 118, Athens Greece, Oct. 11-12, 2001.

Kriveshko et al., U.S. Appl. No. 12/811,268, filed Jun. 30, 2010.

Rohaly et al., U.S. Appl. No. 12/811,237, filed Sep. 27, 2010.

Zhang et al., U.S. Appl. No. 12/811,239, filed Sep. 22, 2010.

Zang et al., U.S. Appl. No. 12/811,242, filed Jun. 30, 2010.

Triggs et al, "Bundle adjustment—a modern synthesis" Vision algorithms: theory and practice (2000) pp. 153-177.

\* cited by examiner

HIERARCHICAL PROCESSING USING IMAGE DEFORMATION

CROSS REFERENCE TO RELATED APPLICATIONS

This application is a national stage filing under 35 U.S.C. 371 of PCT/US2009/030067, filed Jan. 4, 2009, which claims priority to U.S. Provisional Application No. 61/019,159, filed Jan. 4, 2008, the disclosure of which is incorporated by reference in their entirety herein.

FIELD OF INVENTION

This invention relates generally to three-dimensional imaging and more specifically to use of hierarchical image data to improve three-dimensional measurements based upon multiple object images.

BACKGROUND

In one technique for three-dimensional image reconstruction, a number of images or image sets of an object are captured with a camera that travels in a path over the surface of the object. This catalogue of image information can then be used to reconstruct a three-dimensional model of the object based upon the camera path and individual three-dimensional measurements captured along the camera path. In one aspect, the camera employs a number of offset optical channels that capture images from slightly different optical axes. The differences in these offset images contain depth information that can be used to calculate distance from the camera, and in turn to determine the three-dimensional contours of a scanned surface. One computationally intensive part of this technique involves matching features between pairs of images in an image set, which must be repeated many times for each image set in order to find corresponding feature locations in an image pair.

While various techniques are known for correlating features between images, there remains a need for improved techniques suitable for pattern matching in three-dimensional reconstruction.

SUMMARY

A hierarchical pattern matching process is improved for use in three-dimensional reconstruction by calculating a disparity field for low-resolution data, and using this low-resolution disparity field to estimate the disparity field for higher-resolution images. By pre-warping a template according to the estimated disparity field, improved correlation results can be obtained.

In one aspect, a method disclosed herein includes obtaining a first image and a second image of an object from two camera poses; generating a hierarchy of lower-resolution representations of the first image and the second image; obtaining a disparity field that characterizes motion between a lower-resolution representation of the first image and a corresponding one of the lower-resolution representations of the second image; upsampling the disparity field to a higher resolution of the hierarchy to provide an estimated disparity field at the higher resolution; warping a higher-resolution representation of the first image according to the upsampled disparity field to provide a warped image; correlating the warped image to a higher-resolution representation of the second image to obtain a disparity error field; combining the upsampled disparity field and the disparity error field to obtain a higher-resolution disparity field.

The method may include repeating the steps of the method for a next higher-resolution level of the hierarchy. The higher-resolution representation of the first image may be a full resolution image. The lower-resolution representation of the first image may have a smallest size in the hierarchy. The method may include applying the higher-resolution disparity field to a camera model to obtain a three-dimensional surface reconstruction of the object. The hierarchy may include at least one of a three-level pyramid, a four-level pyramid, and a five-level pyramid. The first image and the second image may have a size of 96 pixels in one dimension. The first image and the second image may have a size of 128 pixels in one dimension. The two camera poses may correspond to two offset optical channels in a multi-aperture three-dimensional camera. The two camera poses may correspond to two independent camera positions.

In another aspect, a computer program product disclosed herein includes computer-executable code embodied on a computer-readable medium that, when executing on one or more computing devices, performs the steps of obtaining a first image and a second image of an object from two camera poses; generating a hierarchy of lower-resolution representations of the first image and the second image; obtaining a disparity field that characterizes motion between a lower-resolution representation of the first image and a corresponding one of the lower-resolution representations of the second image; upsampling the disparity field to a higher resolution of the hierarchy to provide an estimated disparity field at the higher resolution; warping a higher-resolution representation of the first image according to the upsampled disparity field to provide a warped image; correlating the warped image to a higher-resolution representation of the second image to obtain a disparity error field; and combining the upsampled disparity field and the disparity error field to obtain a higher-resolution disparity field.

BRIEF DESCRIPTION OF THE DRAWINGS

The invention and the following detailed description of certain embodiments thereof may be understood by reference to the following figures.

DETAILED DESCRIPTION

In the following text, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

The following description details specific scanning technologies and focuses on dental applications of three-dimensional imaging; however, variations, adaptations, and combinations of the methods and systems below will be apparent to one of ordinary skill in the art. For example, while a three-dimensional data acquisition system is described, the following techniques may be employed in any process where differences between pairs of multi-resolution images can be usefully processed. While digital dentistry is one useful application of the improved accuracy that results from the techniques described herein, these techniques may also usefully be employed to refine three-dimensional animation models or three-dimensional scans for machine vision applications. All such variations, adaptations, and combinations are intended to fall within the scope of this disclosure.

In the following description, the term "image" generally refers to a two-dimensional set of pixels forming a two-dimensional view of a subject within an image plane. The term "image set" generally refers to a set of related two-dimensional images that might be resolved into three-dimensional data. The term "point cloud" generally refers to a three-dimensional set of points forming a three-dimensional view of the subject reconstructed from a number of two-dimensional images. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional model", "three-dimensional surface representation", "digital surface representation", "three-dimensional surface map", and the like, as used herein, are intended to refer to any three-dimensional reconstruction of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that a variety of three-dimensional rendering technologies exist, and may be usefully employed with the systems and methods disclosed herein. For example, the systems and methods described herein may usefully employ a holographic display, an autostereoscopic display, an anaglyph display, a head-mounted stereo display, or any other two-dimensional and/or three-dimensional display. As such, rendering as described herein should be interpreted broadly unless a narrower meaning is explicitly provided or otherwise clear from the context.

The term "dental object", as used herein, is intended to refer broadly to subject matter related to dentistry. This may include intraoral structures such as dentition, and more typically human dentition, such as individual teeth, quadrants, full arches, pairs of arches (which may be separate or in occlusion of various types), soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

It will further be understood that terms such as "tool" or "control", when used to describe aspects of a user interface, are intended to refer generally to a variety of techniques that may be employed within a graphical user interface or other user interface to receive user input that stimulates or controls processing including without limitation drop-down lists, radio buttons, cursor and/or mouse actions (selections by point, selections by area, drag-and-drop operations, and so forth), check boxes, command lines, text input fields, messages and alerts, progress bars, and so forth. A tool or control may also include any physical hardware relating to the user input, such as a mouse, a keyboard, a display, a keypad, a track ball, and/or any other device that receives physical input from a user and converts the physical input into an input for use in a computerized system. Thus in the following description the terms "tool", "control" and the like should be broadly construed unless a more specific meaning is otherwise provided or clear from the context.

Figure 1:
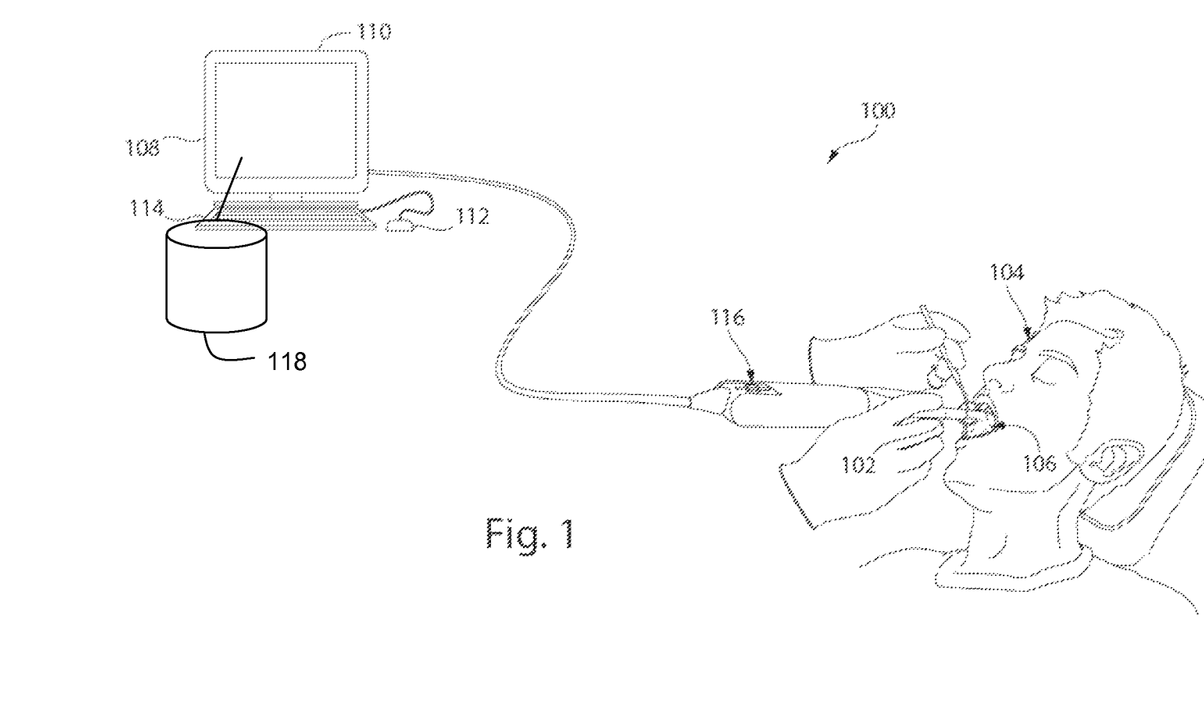
FIG. 1 shows a three-dimensional scanning system.

FIG. 1 depicts a three-dimensional scanning system that may be used with the systems and methods described herein. In general, the system 100 may include a camera 102 that captures images from a surface 106 of an object 104, such as a dental patient, and forwards the images to a computer 108, which may include a display 110 and one or more user-input devices 112, 114 such as a mouse 112 or a keyboard 114. The camera 102 may also include an integrated input or output device 116 such as a control input (e.g., button, touchpad, thumbwheel, etc.) or a display (e.g., LCD or LED display) to provide status information.

The camera 102 may include any camera or camera system suitable for capturing images from which a three-dimensional point cloud or other three-dimensional data may be recovered. For example, the camera 102 may employ a multi-aperture system as disclosed in U.S. Pat. No. 7,372,642 to Rohály et al., the entire content of which is incorporated herein by reference. While Rohály discloses one multi-aperture system, it will be appreciated that any multi-aperture system suitable for reconstructing a three-dimensional point cloud from a number of two-dimensional images may similarly be employed. In one multi-aperture embodiment, the camera 102 may include a plurality of apertures including a center aperture positioned along a center optical axis of a lens that provides a center channel for the camera 102, along with any associated imaging hardware. In such embodiments, the center channel may provide a conventional video image of the scanned subject matter, while a number of axially offset channels yield image sets containing disparity information that can be employed in three-dimensional reconstruction of a surface. In other embodiments, a separate video camera and/or channel may be provided to achieve the same result, i.e., a video of an object corresponding temporally to a three-dimensional scan of the object, preferably from the same perspective, or from a perspective having a fixed, known relationship to the perspective of the camera 102. The camera 102 may also, or instead, include a stereoscopic, triscopic or other multi-camera or other configuration in which a number of cameras or optical paths are maintained in fixed relation to one another to obtain two-dimensional images of an object from a number of different perspectives. The camera 102 may include suitable processing for deriving a three-dimensional point cloud from an image set or a number of image sets, or each two-dimensional image set may be transmitted to an external processor such as contained in the computer 108 described below. In other embodiments, the camera 102 may employ structured light, laser scanning, direct ranging, or any other technology suitable for acquiring three-dimensional data, or two-dimensional data that can be resolved into three-dimensional data. While the techniques described below can usefully employ video data acquired by a video-based three-dimensional scanning system, it will be understood that any other three-dimensional scanning system may be supplemented with a video acquisition system that captures suitable video data contemporaneously with, or otherwise synchronized with, the acquisition of three-dimensional data.

In one embodiment, the camera 102 is a handheld, freely-positionable probe having at least one user-input device 116, such as a button, a lever, a dial, a thumb wheel, a switch, or the like, for user control of the image capture system 100 such as starting and stopping scans. In an embodiment, the camera 102 may be shaped and sized for dental scanning More particularly, the camera 102 may be shaped and sized for intraoral scanning and data capture, such as by insertion into a mouth of an imaging subject and passing over an intraoral surface 106 at a suitable distance to acquire surface data from teeth, gums, and so forth. The camera 102 may, through such a continuous data acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthesis, to ensure proper fitting using a previous scan of corresponding dentition, such as a tooth surface prepared for the prosthesis.

Although not shown in FIG. 1, it will be appreciated that a number of supplemental lighting systems may be usefully employed during image capture. For example, environmental illumination may be enhanced with one or more spotlights illuminating the object 104 to speed image acquisition and improve depth of field (or spatial resolution depth). The camera 102 may also, or instead, include a strobe, a flash, or some other light source to supplement illumination of the object 104 during image acquisition.

The object 104 may be any object, collection of objects, portion of an object, or other subject matter. More particularly with respect to the dental techniques discussed herein, the object 104 may include human dentition captured intraorally from a dental patient's mouth. A scan may capture a three-dimensional representation of some or all of the dentition according to a particular purpose of the scan. Thus the scan may capture a digital model of a tooth, a quadrant of teeth, or a full collection of teeth including two opposing arches, as well as soft tissue or any other relevant intraoral structures. The scan may capture multiple representations, such as a tooth surface before and after preparation for a restoration. As will be noted below, this data may be employed for subsequent modeling such as designing a restoration or determining a margin line for same. During the scan, a center channel of the camera 102 or a separate video system may capture video of the dentition from the point of view of the camera 102. In other embodiments where, for example, a completed fabrication is being virtually test fitted to a surface preparation, the scan may include a dental prosthesis such as an inlay, a crown, or any other dental prosthesis, dental hardware, dental appliance, or the like. The object 104 may also, or instead, include a dental model, such as a plaster cast, a wax-up, an impression, or a negative impression of a tooth, teeth, soft tissue, or some combination of these.

The computer 108 may include, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. In one current embodiment, the system can be operated to capture more than five thousand points per image set in real time using the techniques described herein, and store an aggregated point cloud of several million points. Of course, this point cloud may be further processed to accommodate subsequent data handling, such as by decimating the point cloud data or generating a corresponding mesh of surface data. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the object 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110. In another aspect, the display may include an autostereoscopic display or the like capable of displaying stereo images.

Communications between the computer 108 and the camera 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the camera 102 to the computer 108 may be secured. The computer 108 may generate control signals to the camera 102 which, in addition to image acquisition commands, may include conventional camera controls such as focus or zoom.

In an example of general operation of a three-dimensional image capture system 100, the camera 102 may acquire two-dimensional image sets at a video rate while the camera 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system may employ camera motion estimation to avoid the need for independent tracking of the position of the camera 102. One useful example of such a technique is described in commonly-owned U.S. application Ser. No. 11/270,135, filed on Nov. 9, 2005, the entire content of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In general, the display 110 may be operatively coupled to, and capable of receiving display signals from, the computer 108. This display may include a CRT or flat panel monitor, a three-dimensional display (such as an anaglyph display), an autostereoscopic three-dimensional display or any other suitable two-dimensional or three-dimensional rendering hardware. In some embodiments, the display may include a touch screen interface using, for example capacitive, resistive, or surface acoustic wave (also referred to as dispersive signal) touch screen technologies, or any other suitable technology for sensing physical interaction with the display 110.

The system 100 may include a computer-usable or computer-readable medium. The computer-usable medium 118 may include one or more memory chips (or other chips, such as a processor, that include memory), optical disks, magnetic disks or other magnetic media, and so forth. The computer-usable medium 118 may in various embodiments include removable memory (such as a USB device, tape drive, external hard drive, and so forth), remote storage (such as network attached storage), volatile or non-volatile computer memory, and so forth. The computer-usable medium 118 may contain computer-readable instructions for execution by the computer 108 to perform the various processes described herein. The computer-usable medium 118 may also, or instead, store data received from the camera 102, store a three-dimensional model of the object 104, store computer code for rendering and display, and so forth.

Figure 2:
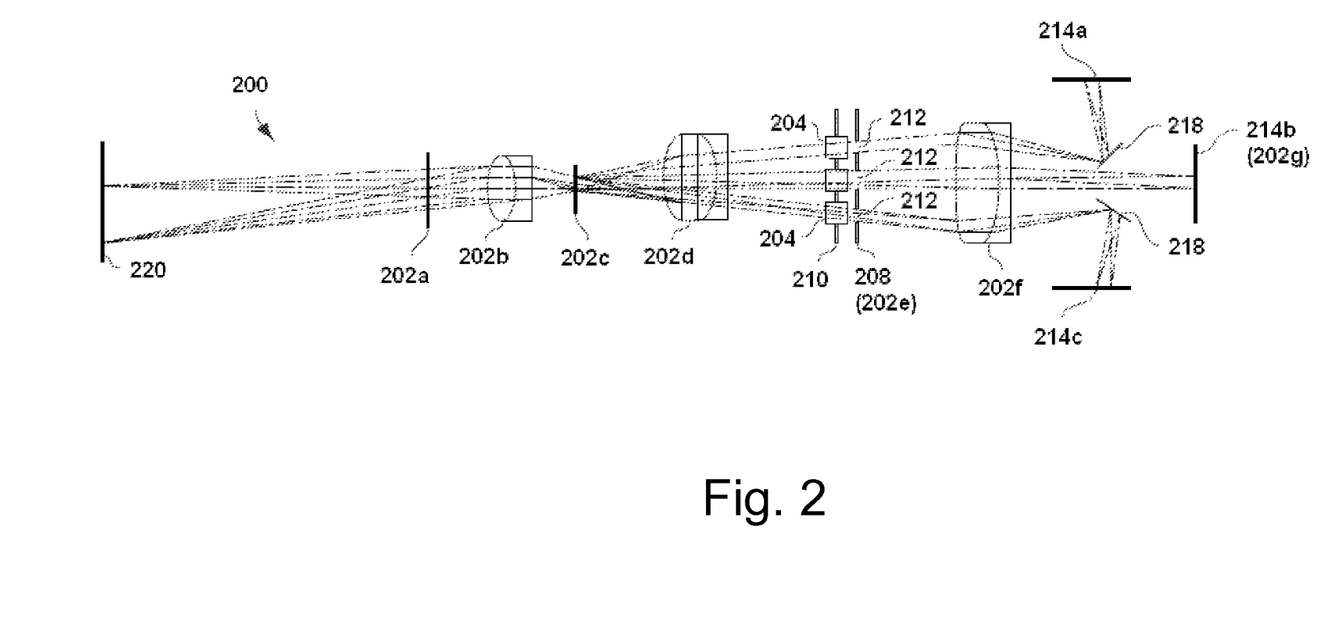
FIG. 2 shows a schematic diagram of an optical system for a three-dimensional camera.

FIG. 2 depicts an optical system 200 for a three-dimensional camera that may be used with the systems and methods described herein, such as for the camera 102 described above with reference to FIG. 1.

The optical system 200 may include a primary optical facility 202, which may be employed in any kind of image processing system. In general, a primary optical facility refers herein to an optical system having one optical channel. Typically, this optical channel shares at least one lens, and has a shared image plane within the optical system, although in the following description, variations to this may be explicitly described or otherwise clear from the context. The optical system 200 may include a single primary lens, a group of lenses, an object lens, mirror systems (including traditional mirrors, digital mirror systems, digital light processors, or the like), confocal mirrors, and any other optical facilities suitable for use with the systems described herein. The optical system 200 may be used, for example in a stereoscopic or other multiple image camera system. Other optical facilities may include holographic optical elements or the like. In various configurations, the primary optical facility 202 may include one or more lenses, such as an object lens (or group of lenses) 202*b*, a field lens 202*d*, a relay lens 202*f*, and so forth. The object lens 202*b* may be located at or near an entrance pupil 202*a* of the optical system 200. The field lens 202*d* may be located at or near a first image plane 202*c* of the optical system 200. The relay lens 202*f* may relay bundles of light rays within the optical system 200. The optical system 200 may further include components such as aperture elements 208 with one or more apertures 212, a refocusing facility 210 with one or more refocusing elements 204, one or more sampling facilities 218, and/or a number of sensors 214*a*, 214*b*, 214*c*.

The optical system 200 may be designed for active wavefront sampling, which should be understood to encompass any technique used to sample a series or collection of optical data from an object 220 or objects, including optical data used to help detect two-dimensional or three-dimensional characteristics of the object 220, using optical data to detect motion, using optical data for velocimetry or object tracking, or the like. Further details of an optical system that may be employed as the optical system 200 of FIG. 2 are provided in U.S. Pat. No. 7,372,642, the entire content of which is incorporated herein by reference. More generally, it will be understood that, while FIG. 2 depicts one embodiment of an optical system 200, numerous variations are possible.

Figure 3:
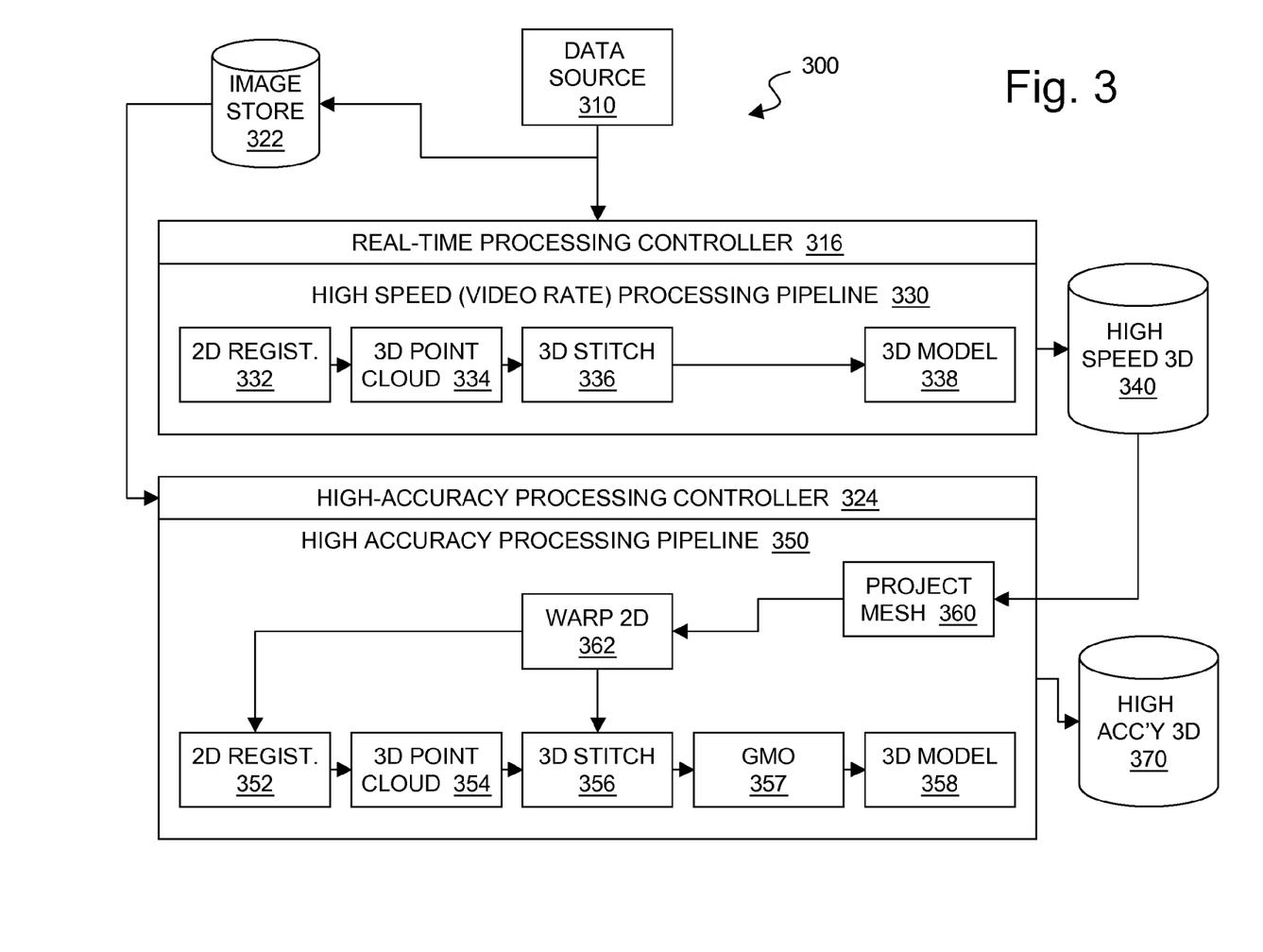
FIG. 3 shows a processing pipeline for obtaining three-dimensional data from a video camera.

FIG. 3 shows a three-dimensional reconstruction system 300 employing a high-speed pipeline and a high-accuracy pipeline. In general, the high-speed processing pipeline 330 aims to provide three-dimensional data in real time, such as at a video frame rate used by an associated display, while the high-accuracy processing pipeline 350 aims to provide the highest accuracy possible from camera measurements, subject to any external computation or time constraints imposed by system hardware or an intended use of the results. A data source 310 such as the camera 102 described above provides image data or the like to the system 300. The data source 310 may for example include hardware such as LED ring lights, wand sensors, a frame grabber, a computer, an operating system and any other suitable hardware and/or software for obtaining data used in a three-dimensional reconstruction. Images from the data source 310, such as center channel images containing conventional video images and side channels containing disparity data used to recover depth information may be passed to the real-time processing controller 316. The real-time processing controller 316 may also provide camera control information or other feedback to the data source 310 to be used in subsequent data acquisition or for specifying data already obtained in the data source 310 that is needed by the real-time processing controller 316. Full resolution images and related image data may be retained in a full resolution image store 322. The stored images may, for example, be provided to the high-accuracy processing controller 324 during processing, or be retained for image review by a human user during subsequent processing steps.

The real-time processing controller 316 may provide images or frames to the high-speed (video rate) processing pipeline 330 for reconstruction of three-dimensional surfaces from the two-dimensional source data in real time. In an exemplary embodiment, two-dimensional images from an image set such as side channel images, may be registered by a two-dimensional image registration module 332. Based on the results of the two-dimensional image registration, a three-dimensional point cloud generation module 334 may create a three-dimensional point cloud or other three-dimensional representation. The three-dimensional point clouds from individual image sets may be combined by a three-dimensional stitching module 336. Finally, the stitched measurements may be combined into an integrated three-dimensional model by a three-dimensional model creation module 338. The resulting model may be stored as a high-speed three-dimensional model 340.

The high-accuracy processing controller 324 may provide images or frames to the high-accuracy processing pipeline 350. Separate image sets may have two-dimensional image registration performed by a two-dimensional image registration module 352. Based on the results of the two-dimensional image registration a three-dimensional point cloud or other three-dimensional representation may be generated by a three-dimensional point cloud generation module 354. The three-dimensional point clouds from individual image sets may be connected using a three-dimensional stitching module 356. Global motion optimization, also referred to herein as global path optimization or global camera path optimization, may be performed by a global motion optimization module 357 in order to reduce errors in the resulting three-dimensional model 358. In general, the path of the camera as it obtains the image frames may be calculated as a part of the three-dimensional reconstruction process. In a post-processing refinement procedure, the calculation of camera path may be optimized—that is, the accumulation of errors along the length of the camera path may be minimized by supplemental frame-to-frame motion estimation with some or all of the global path information. Based on global information such as individual frames of data in the image store 322, the high-speed three-dimensional model 340, and intermediate results in the high-accuracy processing pipeline 350, the high-accuracy model 370 may be processed to reduce errors in the camera path and resulting artifacts in the reconstructed model. As a further refinement, a mesh may be projected onto the high-speed model by a mesh projection module 360. The resulting images may be warped or deformed by a warping module 362. Warped images may be utilized to ease alignment and stitching between images, such as by reducing the initial error in a motion estimate. The warped images may be provided to the two-dimensional image registration module 352. The feedback of the high-accuracy three-dimensional model 370 into the pipeline may be repeated until some metric is obtained, such as a stitching accuracy or a minimum error threshold.

Figure 4:
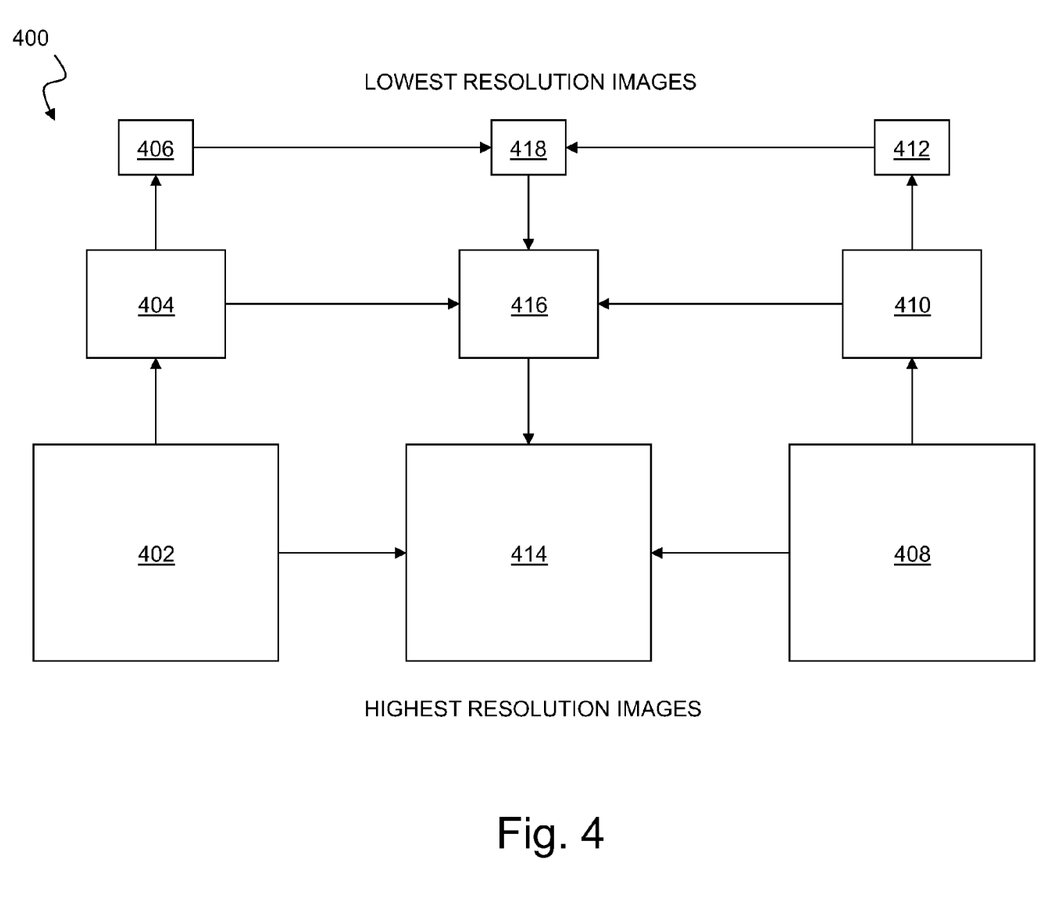
FIG. 4 shows a multi-resolution image hierarchy.

FIG. 4 shows a multi-resolution image hierarchy. In general, a hierarchy 400 (also referred to as a pyramid) of various resolution images is prepared from a full resolution source image 402, including any number of lower-resolution images 404 and a lowest-resolution image 406. In a multi-aperture system such as any of those described above, each full resolution source image 402 (e.g., from a side channel of the camera) may have one or more corresponding full resolution source images 408 captured from a fixed, known location relative to the full resolution image 402. This corresponding full resolution source image 408 may also be pre-processed into any number of lower-resolution images 410 and a lowest-resolution image 412. As generally described below, a disparity field image 418 may be obtained for the lowest-resolution images 406, 412 that encodes differences between the image content of the images 406, 412. This disparity field image 418 may be used to estimate higher-resolution disparity fields 416, 414, which can simplify and/or refine correspondence and disparity determinations for the higher-resolution content.

Figure 5:
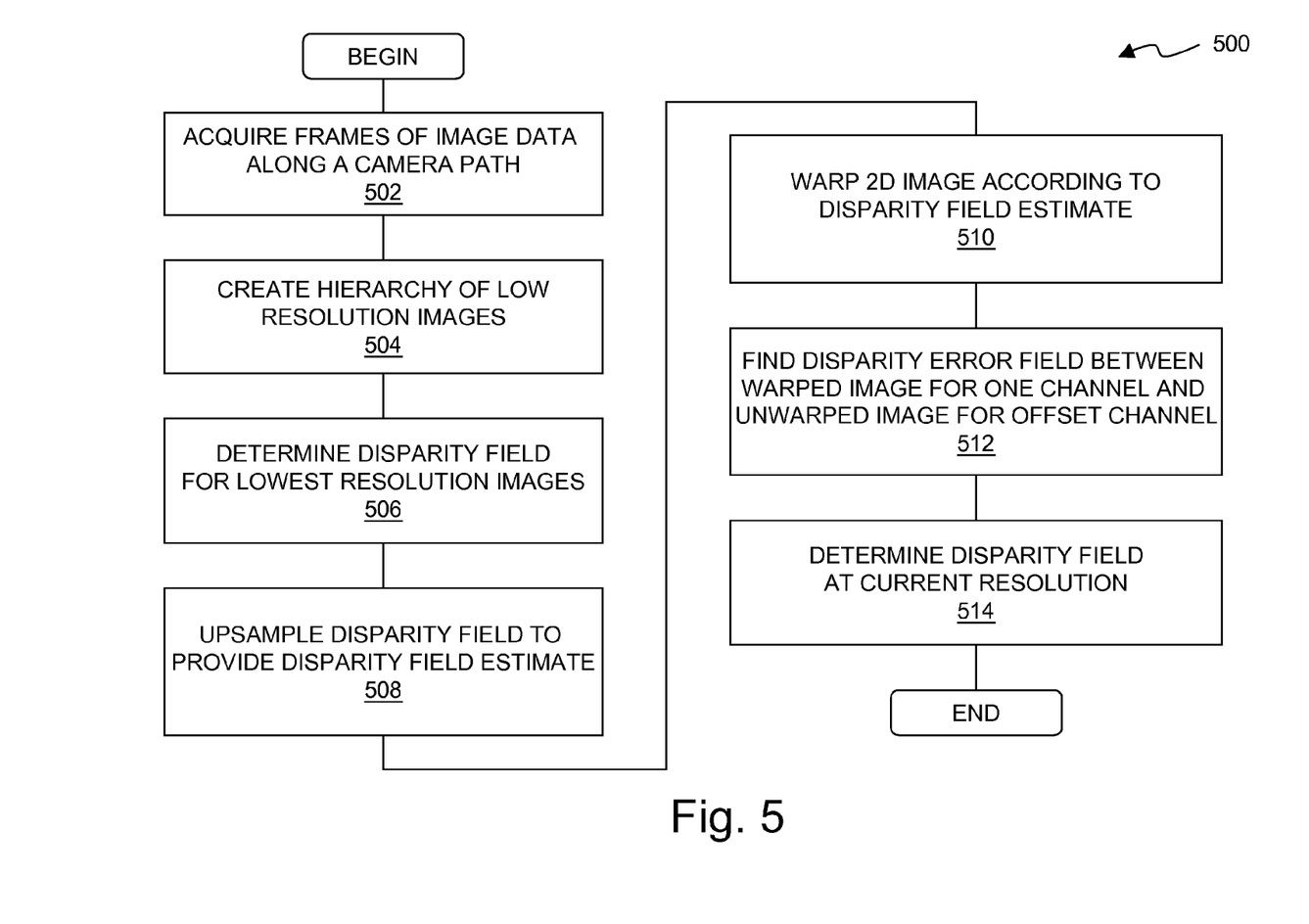
FIG. 5 shows a method for hierarchical processing in three-dimensional reconstruction.

FIG. 5 shows a method for hierarchical processing in three-dimensional reconstruction. As shown in step 502, the process 500 may begin with acquiring frames of image data along a camera path using, for example, a multi-aperture camera such as that described above. This may include image pairs from two offset channels of the camera along with a center channel that encodes conventional, undistorted images, all at a full resolution of the camera. By way of example and not limitation, this may include 128×128 pixel square images (i.e., having 128 pixels in each dimension), or any other dimensions selected according to processing constraints, imaging hardware, or the like. The camera poses for two offset channels of a multi-aperture camera are dependent on one another. That is, these poses have a fixed, known spatial relationship with one another. While the hierarchical processing techniques described herein may be usefully employed in this context, it will be understood that this technique may be more broadly applicable to any motion-based recovery of three-dimensional data. For example, two images capture from independent camera poses, such as a single aperture camera in two positions, may be processed to locate disparities for any common subject matter between the images, and the process 500 described herein may be usefully employed to recover a disparity field from such images.

As shown in step 504, a hierarchy of lower-resolution images may be obtained based on the full resolution images. This may include, any suitable technique known in the art for compression, downsampling, and the like that sufficiently preserves two-dimensional spatial information to accommodate comparison of the lower-resolution images. By way of example and not of limitation, the hierarchy may include three to five levels of progressively lower-resolution images, or a lowest resolution of 32 pixels, 16 pixels, or 8 pixels.

As shown in step 506, a disparity field may be determined for the lowest-resolution images in the hierarchy. This disparity field may encode differences such as displacement of features, between the two offset images of the camera based upon the low-resolution data. Numerous techniques are known for locating and characterizing disparities in two-dimensional images, any of which may be suitably adapted to use in step 506.

As shown in step 508, the lowest-resolution disparity field may be upsampled using any suitable technique to the next hierarchical level, e.g., a level having twice the resolution. This may provides an estimate of the higher-resolution disparity field. While doubling resolution is one useful step size for processing as described herein, it will be understood that upsampling to other image sizes may also be employed without departing from the scope of this disclosure.

As shown in step 510, the disparity field estimate may be applied to warp one of the higher-resolution, two-dimensional images from the camera. In general, this step applies motion information from the lower level to a higher resolution image. This may be implemented, for example, as a linear interpolation of the disparity field at the higher resolution.

As shown in step 512, a disparity field at the upsampled resolution level may be obtained by comparing the warped image from one channel of the camera to an unwarped image of a corresponding offset channel. As a significant advantage, this approach may align the processing mesh for the two images in an image pair, and may provide higher-resolution processing for disparity data at that level. The warped image from one channel and the unwarped image from the other channel may be correlated using any suitable techniques to recover a disparity field describing motion between the two images. Unless the disparity field estimate is perfectly accurate at the higher resolution, some residual motion will be present after one of the images is warped according to the estimate. This difference may be recovered on a pixel-by-pixel basis for the processing mesh using any suitable technique for recovering motion from multiple two-dimensional images, and the result may be used as a disparity error field to refine the disparity estimate from the lower resolution image.

As shown in step 514, the disparity field at the current processing resolution may be determined by combining the estimated disparity field and the disparity field error. Because the relationship between values in the estimated disparity field and the disparity field error may be complex and non-uniform across a particular image set, the disparity field error may be incorporated into the disparity field estimate indirectly, e.g., by using the error values to provide a half-pixel refinement of estimated values, or using any other suitable technique. This approach may reduce the need for accurate peak estimation (shape or position) to achieve sub-pixel correlation results. The resulting disparity field at full resolution may be used, for example to recover a three-dimensional measurement from a current camera location. For example, a camera model may be employed to relate the disparity values in the disparity field to depth measurements at corresponding locations in the processing mesh.

It will be understood that the process 500 may be repeated for any number of levels in a hierarchy of images. For example, the process 500 may be repeated for each hierarchical level beginning at a lowest-resolution image and ending with a refined disparity field for a highest-resolution image. As a significant advantage, this approach reduces the need to perform full-resolution correlation to directly recover the disparity field for full resolution images. It will be further understood that the process 500 may be repeated any number of times across a catalogue of image sets in a three-dimensional scan, and may more specifically be performed for each image set from which three-dimensional data is recovered. In certain embodiments, the process 500 may be employed to refine a high-accuracy three-dimensional model. In other embodiments, the process 500 may be implemented in a real time three-dimensional imaging pipeline. It will further be understood that numerous variations, additions, deletions, and other modifications of steps are possible, including changes to the number of levels of the hierarchy, the resolution of images, the addition of center channel information, and so forth, all without departing from the scope of this disclosure.

It will be appreciated that any of the above system and/or methods may be realized in hardware, software, or any combination of these suitable for the data acquisition and modeling technologies described herein. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. Thus in one aspect there is disclosed herein a method comprising computer executable code that, when executing on one or more computing devices, performs any and/or all of the steps described above. At the same time, processing may be distributed across devices such as a camera and/or computer and/or fabrication facility and/or dental laboratory and/or server in a number of ways or all of the functionality may be integrated into a dedicated, standalone device. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method comprising the steps of:
   obtaining a first image and a second image of an object from two camera poses;
   generating a hierarchy of lower-resolution representations of the first image and the second image;
   obtaining a disparity field that characterizes motion between a lower-resolution representation of the first image and a corresponding one of the lower-resolution representations of the second image;
   upsampling the disparity field to a higher resolution of the hierarchy to provide an estimated disparity field at the higher resolution;
   warping a higher-resolution representation of the first image by distorting the higher-resolution representation according to the upsampled disparity field to align a processing mesh for the higher-resolution representation of the first image with a higher-resolution representation of the second image, thereby providing a warped image;
   correlating the warped image to the higher-resolution representation of the second image to obtain a disparity error field; and
   combining the upsampled disparity field and the disparity error field to obtain a higher-resolution disparity field.

2. The method of claim 1 further comprising repeating the steps of the method for a next higher-resolution level of the hierarchy.

3. The method of claim 1 wherein the higher-resolution representation of the first image is a full resolution image.

4. The method of claim 1 wherein the lower-resolution representation of the first image has a smallest size in the hierarchy.

5. The method of claim 1 further comprising applying the higher-resolution disparity field to a camera model to obtain a three-dimensional surface reconstruction of the object.

6. The method of claim 1 wherein the hierarchy includes at least one of a three-level pyramid, a four-level pyramid, and a five-level pyramid.

7. The method of claim 1 wherein the first image and the second image have a size of 96 pixels in one dimension.

8. The method of claim 1 wherein the first image and the second image have a size of 128 pixels in one dimension.

9. The method of claim 1 wherein the two camera poses correspond to two offset optical channels in a multi-aperture three-dimensional camera.

10. The method of claim 1 wherein the two camera poses correspond to two independent camera positions.

11. A computer program product comprising computer-executable code embodied on a non-transitory computer-readable medium that, when executing on one or more computing devices, performs the steps of:
- obtaining a first image and a second image of an object from two camera poses;
- generating a hierarchy of lower-resolution representations of the first image and the second image;
- obtaining a disparity field that characterizes motion between a lower-resolution representation of the first image and a corresponding one of the lower-resolution representations of the second image;
- upsampling the disparity field to a higher resolution of the hierarchy to provide an estimated disparity field at the higher resolution;
- warping a higher-resolution representation of the first image by distorting the higher-resolution representation according to the upsampled disparity field to align a processing mesh for the higher-resolution representation of the first image with a higher-resolution representation of the second image, thereby providing a warped image;
- correlating the warped image to the higher-resolution representation of the second image to obtain a disparity error field; and
- combining the upsampled disparity field and the disparity error field to obtain a higher-resolution disparity field.

12. The computer program product of claim 11 further comprising code for repeating the steps for a next higher-resolution level of the hierarchy.

13. The computer program product of claim 11 wherein the higher-resolution representation of the first image is a full resolution image.

14. The computer program product of claim 11 wherein the lower-resolution representation of the first image has a smallest size in the hierarchy.

15. The computer program product of claim 11 further comprising code for performing the step of applying the higher-resolution disparity field to a camera model to obtain a three-dimensional surface reconstruction of the object.

16. The computer program product of claim 11 wherein the hierarchy includes at least one of a three-level pyramid, a four-level pyramid, and a five-level pyramid.

17. The computer program product of claim 11 wherein the first image and the second image have a size of 96 pixels in one dimension.

18. The computer program product of claim 11 wherein the first image and the second image have a size of 128 pixels in one dimension.

19. The computer program product of claim 11 wherein the two camera poses correspond to two offset optical channels in a multi-aperture three-dimensional camera.

20. The computer program product of claim 11 wherein the two camera poses correspond to two independent camera positions.

* * * * *